(12) United States Patent
Greter et al.

(10) Patent No.: US 7,682,334 B2
(45) Date of Patent: Mar. 23, 2010

(54) BREAST COVER INSERT

(75) Inventors: Andy Greter, Steinhausen (CH); Brian Silver, Cary, IL (US)

(73) Assignee: Medela Holding AG, Baar (CH)

( * ) Notice: Subject to any disclaimer, the term of this patent is extended or adjusted under 35 U.S.C. 154(b) by 805 days.

(21) Appl. No.: 10/362,982

(22) PCT Filed: Aug. 28, 2001

(86) PCT No.: PCT/CH01/00523

§ 371 (c)(1),
(2), (4) Date: Jul. 14, 2003

(87) PCT Pub. No.: WO02/17993

PCT Pub. Date: Mar. 7, 2002

(65) Prior Publication Data

US 2004/0029486 A1 Feb. 12, 2004

(30) Foreign Application Priority Data

Aug. 28, 2000 (EP) .................................. 00118599

(51) Int. Cl.
*A61M 1/06* (2006.01)
(52) U.S. Cl. ....................................................... 604/74
(58) Field of Classification Search .............. 604/74–76; 128/889, 890; 450/36–39
See application file for complete search history.

(56) References Cited

U.S. PATENT DOCUMENTS

| 146,805 | A | * | 1/1874 | Cox | ............... | 450/38 |
|---|---|---|---|---|---|---|
| RE14,024 | E | * | 11/1915 | Whitmarsh | ............... | 607/114 |
| 4,263,912 | A | * | 4/1981 | Adams | ............... | 604/75 |
| 4,607,596 | A | | 8/1986 | Whittlestone et al. | | |
| 4,673,388 | A | | 6/1987 | Schlensog et al. | | |
| 5,050,595 | A | * | 9/1991 | Krafft | ............... | 607/108 |
| 5,100,406 | A | * | 3/1992 | Panchula | ............... | 604/74 |
| 5,149,336 | A | | 9/1992 | Clarke et al. | | |
| 5,776,177 | A | * | 7/1998 | MacWhinnie et al. | ............... | 607/108 |
| 5,885,246 | A | * | 3/1999 | Ford | ............... | 604/74 |
| 5,897,580 | A | * | 4/1999 | Silver | ............... | 607/108 |
| 6,273,868 | B1 | * | 8/2001 | Nordvik | ............... | 604/74 |
| 6,358,226 | B1 | * | 3/2002 | Ryan | ............... | 604/74 |
| 2003/0162479 | A1 | * | 8/2003 | Tonsor | ............... | 450/54 |

FOREIGN PATENT DOCUMENTS

| JP | 38-28586 | | 12/1963 |
|---|---|---|---|
| JP | 62-1634 | * | 1/1987 |
| WO | WO 0010625 A1 | * | 3/2000 |
| WO | 00 47068 | | 8/2000 |

* cited by examiner

*Primary Examiner*—Nicholas D Lucchesi
*Assistant Examiner*—Theodore J Stigell
(74) *Attorney, Agent, or Firm*—McDonnell Boehnen Hulbert & Berghoff LLP

(57) ABSTRACT

The invention relates to a breast cover insert comprising a truncated conical frame (1), which is provided as a double wall (1, 6) while forming a closed space (7), whereby at least the inner wall (6) can be elastically deformed, and the space (7) contains a preferably elastically deformable medium.

6 Claims, 1 Drawing Sheet

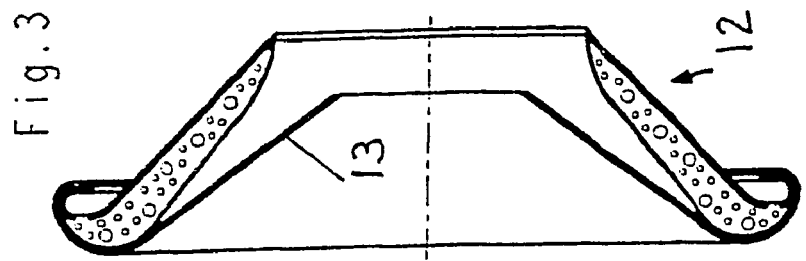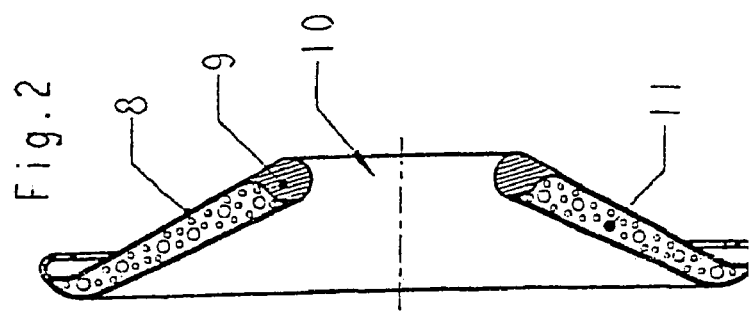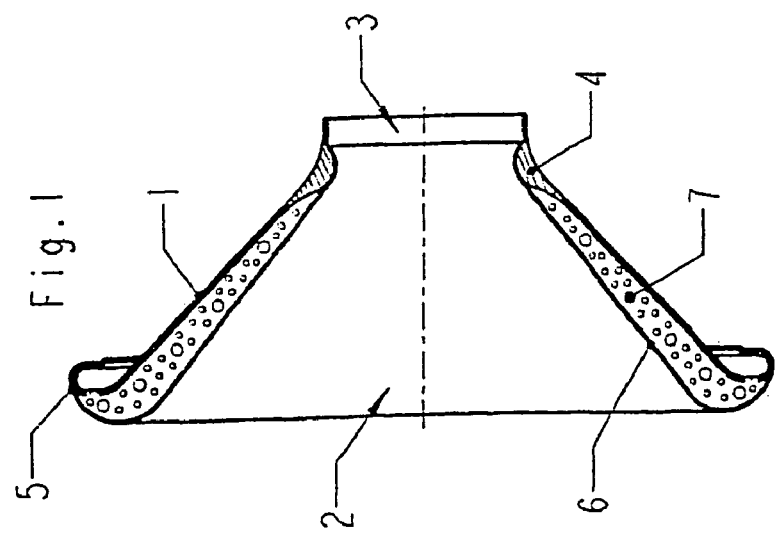

BREAST COVER INSERT

The present invention relates to a breast cover insert for breast pumps, with a substantially truncated cone shaped frame with a large rear opening and a small front opening which is adapted to abut the areola of a female breast.

Breast cover inserts of the kind described above are known since several years and serve for a adjusting of the cover to different breast sizes and a improved stimulation of the output of the mothers milk.

It has been object of the present invention to further optimise the breast cover inserts by a special design or special structure of the insert and to render their application still more comfortable.

This object has been solved by a breast cover insert of the kind defined above in accordance with the invention by the features of the characterising portion of claim 1.

The effectiveness and the comfort of the application by the subject of the invention are still more substantially increased in comparison with the prior art.

Specific embodiments of the subject of the invention are defined in the dependent claims.

In the following, the invention will be explained somewhat more in detail with reference to the embodiments illustrated in the drawing.

There is shown in:

FIG. 1 a vertical section through a first embodiment of a insert in accordance with the invention;

FIG. 2 a variant, also in vertical section; and

FIG. 3 a further variant with a supplementary foil.

FIG. 1 of the drawing illustrates a truncated cone shaped breast cover insert with a frame 1 (of plastic material or elastomeric material) with a rear large opening 2 and a front small opening 3. A heightening (thickening) 4 is foreseen at the radially inner side of the small opening 3, which serves for the placing onto the areola of the female breast (for stimulation). A elastic inner wall 6 (e.g. PU—foil) extends between this heightening 4 and the edge 5 of the large opening 2 and forms together with the frame 1 a chamber 7 which contains a deformable medium (Gas, e.g. air; a thickened liquid; a gel; silicon). This measure adds substantially to the increase of the comfort during the application.

FIG. 2 illustrates a variant of the breast cover insert, with a in comparison with the embodiment according to FIG. 1 slightly different design of the frame 8. It consists of a truncated cone shaped hollow profile part of a elastic material, whereby also here the heightening 9 at the small opening 10 and the filling of the chamber 11 are present.

FIG. 3 illustrates a further variant of the breast cover insert 12 with a substantially same design as the embodiments according to FIG. 1 or 2, which includes in place of the heightening (4 or 9, resp.) foreseen at the small frame opening a elastic supplementary insert 13 (silicon foil), which also serves for the "centering" of the breast and the stimulation. This supplementary insert 13 allows a optimal positioning of the nipple and can prevent a undesired flowing down of milk after removing the cover (Catching the milk in the space between the insert frame 1, 8 and the supplementary foil 13.

The invention claimed is:

1. A breast cover insert for a breastpump, the breast cover comprising:
    a frame, the frame having a substantially truncated cone shape with a large rear opening and a small front opening which is adapted to abut the areola of a female breast; and
    the frame having a frame wall;
    wherein the frame wall is designed as a double wall with an inner wall and an outer wall;
    the inner wall extending continuously from the small front opening to the large rear opening and curving around the large rear opening so as to form an annular lip having an annular channel that faces the outer wall, the lip adapted to attach to the breastpump;
    wherein at least the inner wall is elastically deformable;
    wherein the double wall forms a closed chamber;
    wherein the closed chamber is filled with a filling medium which is deformable; and
    wherein said insert is sized and shaped to be removably received by the breastpump so as to contact a female breast when so received.

2. A breast cover insert according to claim 1, wherein the deformable medium of the chamber includes one or more of a gas, air, a thickened liquid, a gel or silicone.

3. A breast cover insert according to claim 1 or 2, wherein a radially inwards projecting circumferential heightening is arranged at an inner side of the smaller front opening.

4. A breast cover insert according to claim 3, wherein the heightening is designed as a deformable chamber.

5. A breast cover insert according to claim 3, wherein the elastically deformable inner wall of the frame extends between an edge of the larger opening and an inner edge of the heightening at the smaller opening.

6. A breast cover insert according to claim 1 or 2, wherein an elastic centering foil is located within the insert which is detachable or firmly connected to the frame.

* * * * *